US010408726B2

(12) United States Patent
Sugasawa

(10) Patent No.: US 10,408,726 B2
(45) Date of Patent: *Sep. 10, 2019

(54) PARTICLE SIZE DISTRIBUTION MEASURING APPARATUS

(71) Applicant: HORIBA, Ltd., Kyoto (JP)

(72) Inventor: Hirosuke Sugasawa, Kyoto (JP)

(73) Assignee: HORIBA, LTD., Kyoto (JP)

( * ) Notice: Subject to any disclaimer, the term of this patent is extended or adjusted under 35 U.S.C. 154(b) by 579 days.

This patent is subject to a terminal disclaimer.

(21) Appl. No.: 14/311,804

(22) Filed: Jun. 23, 2014

(65) Prior Publication Data

US 2014/0379289 A1 Dec. 25, 2014

(30) Foreign Application Priority Data

Jun. 24, 2013 (JP) .................................. 2013-132140

(51) Int. Cl.
*G01N 15/02* (2006.01)
(52) U.S. Cl.
CPC .................................. *G01N 15/0205* (2013.01)
(58) Field of Classification Search
CPC .................................................. G01N 15/0205
See application file for complete search history.

(56) References Cited

U.S. PATENT DOCUMENTS

| 9,243,989 B2 * | 1/2016 | Sugasawa | G01N 15/0211 |
| 2001/0035954 A1 | 11/2001 | Rahn et al. | |
| 2002/0036776 A1 | 3/2002 | Shimaoka | |

FOREIGN PATENT DOCUMENTS

| GB | 2478183 A | 8/2011 |
| JP | 02024533 A | 1/1990 |
| JP | 02203247 A | 8/1990 |
| JP | 04191640 A | 7/1992 |
| JP | 05324700 A | 12/1993 |
| JP | 06348746 A | 12/1994 |
| JP | 09126984 A | 5/1997 |
| JP | 10177591 A | 6/1998 |
| JP | 10197439 A | 7/1998 |

(Continued)

OTHER PUBLICATIONS

Takeshi Kinoshita, "The method to determine the optimum refractive index parameter in the laser diffraction and scattering method", Jun. 11, 2001, Advanced Powder Technology, vol. 12, No. 4, pp. 589-602.*

(Continued)

*Primary Examiner* — Mischita L Henson
(74) *Attorney, Agent, or Firm* — Cantor Colburn LLP

(57) ABSTRACT

In order to reduce a calculation time of a particle size distribution, a particle size distribution measuring apparatus includes: a light source for irradiating light to particles to be measured; a plurality of photodetectors for detecting light intensities of diffracted/scattered lights caused by the irradiation of the light; and an operation part for receiving light intensity signals outputted from the respective photodetectors and calculating a particle size distribution of the particles based on the fact that a vector s is represented by a predetermined expression including a product of a vector q and a coefficient matrix K, and the operation part is configured to compute in parallel and calculate at least two elements of the elements of the coefficient matrix K.

7 Claims, 7 Drawing Sheets

(56) References Cited

FOREIGN PATENT DOCUMENTS

| JP | 10222487 | A | | 8/1998 | | |
|---|---|---|---|---|---|---|
| JP | 11183357 | A | | 7/1999 | | |
| JP | 2004184134 | A | | 7/2004 | | |
| JP | 2008164539 | A | | 7/2008 | | |
| JP | 4835389 | B2 | * | 12/2011 | ............. | G01N 15/02 |

OTHER PUBLICATIONS

W J. Wiscombe, "Mie Scattering Calculations : Advances in Technique and Fast, Vector-Speed Computer Codes", NCAR technical note, Aug. 1996 (NB-updating a 1979 version of the same publication).
Search Report corresponding to UK Patent Application No. GB1411128.0; dated Dec. 19, 2014.
Japanese Office Action corresponding to Application No. JP2013-132140; dated Mar. 28, 2017.
Section 21 Observation for corresponding UK patent application No. GB2517566A; Issue date of Jun. 19, 2015.
UK Search Report for corresponding Application No. GB1411129.8; dated Dec. 19, 2014.
W. J. Wiscombe, "Improved Mie scattering algorithms", Applied Optics, May 1, 1980, vol. 19, pp. 1505-1509.
JPO Notification of Reasons for Refusal corresponding to Application No. 2017-214108; Dated Dec. 13, 2018.

* cited by examiner

PARTICLE SIZE DISTRIBUTION MEASURING APPARATUS

CROSS REFERENCE TO RELATED APPLICATIONS

The present invention claims priority under 35 U.S.C. § 119 to Japanese Application No. 2013-132140 filed Jun. 24, 2013, the entire content of which is incorporated herein by reference.

TECHNICAL FIELD

The present invention relates to a particle size distribution measuring apparatus for calculating a particle size distribution of particles based on a light intensity pattern of diffracted light and/or scattered light (also, referred to as "diffracted/scattered light", hereinafter) caused by irradiation of light to the particles to be measured.

BACKGROUND ART

As disclosed in Patent Literature 1, a particle size distribution measuring apparatus of this kind is intended to detect diffracted/scattered light by a plurality of photodetectors and calculate a particle size distribution based on the following Expression (1) using a light intensity pattern vector obtained by a value of a light intensity signal outputted from each of the photodetectors.

[Equation 1]
$$s = Kq \quad (1)$$

Here, s is a vector representing a light intensity pattern at every angle of diffracted/scattered light obtained from a value of a light intensity signal outputted from each of the photodetectors, q is a vector representing a particle size distribution of the particles to be measured, and K is a coefficient matrix for converting the particle size distribution vector to the light intensity pattern vector.

CITATION LIST

Patent Literature

Patent Literature 1: JPA 2008-164539

SUMMARY OF INVENTION

Technical Problem

By the way, the coefficient matrix K is determined depending on physical properties such as a refractive index of the particles, particle sizes and arrangement positions of the photodetectors. Therefore, in order to calculate the particle size distribution based on the above Expression (1), it is essentially necessary to previously calculate the coefficient matrix K.

However, in the conventional technic, since each of elements of the coefficient matrix K is obtained one by one based on such as a Mie scattering theory, it takes considerable time for calculation of the coefficient matrix K.

Therefore, the present invention has been made in consideration of solving the problem and its essential object is to reduce a calculation time of a particle size distribution by reducing the calculation time of the coefficient matrix K.

Solution to Problem

That is, a particle size distribution measuring apparatus according to the present invention includes: a light source for irradiating light to particles to be measured; a plurality of photodetectors for detecting light intensities of diffracted/scattered lights caused by the irradiation of the light; and an operation part for receiving light intensity signals outputted from the respective photodetectors and calculating a particle size distribution of the particles based on the fact that a vector s is represented by a predetermined expression including a product of a vector q and a coefficient matrix K, and the operation part is adapted to compute in parallel and calculate at least two elements of elements of the coefficient matrix K. Here, the vector s is a vector representing a light intensity pattern at every angle of the diffracted/scattered lights obtained from values of the light intensity signals outputted from the respective photodetectors, the vector q is a vector representing the particle size distribution of the particles to be measured, and the coefficient matrix K is a matrix for converting the vector q to the vector s.

As the predetermined expression, for example, the Expression (1) mentioned above or an expression including a term representing such as, for example, a noise added to this Expression (1) can be exemplified.

With this configuration, since the elements of the coefficient matrix K are computed in parallel and calculated, the calculation time of the coefficient matrix K can be reduced compared to a case of calculating each of the elements one by one. Thus, it is possible to reduce a time required to calculate the particle size distribution.

As a specific aspect of the present invention, it is exemplified that the operation part computes in parallel and calculates at least two elements included in one row or at least two elements included in one column among the elements of the coefficient matrix K.

Further, in order to reduce the calculation time of the coefficient matrix K, it is preferable that the operation part calculates values of a plurality of parameters used for calculating one element of the coefficient matrix K and stores at least one of the values to be used for calculating another element of the coefficient matrix K.

Here, the coefficient matrix K is represented by Expression (2) as follows:

[Equation 2]
$$K = \begin{pmatrix} k_{11} & k_{12} & \ldots & k_{1y} \\ k_{21} & & & \vdots \\ \vdots & & & \vdots \\ k_{x1} & \ldots & \ldots & k_{xy} \end{pmatrix} \quad (2)$$

Here, x is a number of the photodetectors, and y is a number of divisions of the particle size range to be measured.

In this coefficient matrix K, when calculating the elements belonging to the same row, the parameter that depends on the spread angle of the diffracted/scattered lights can be used in common, and when calculating the elements belonging to the same column, the parameters that depend on the refractive indexes of the particles and particle sizes can be used in common.

Therefore, as another specific aspect of the present invention, it is exemplified that the operation part calculates an element of a position where a certain row and a certain column intersect using the values of the plurality of parameters stored at a time of calculating the elements included in the row and the values of the plurality of parameters stored at a time of calculating the elements included in the column among the elements of the coefficient matrix K.

Further, a particle size distribution measuring apparatus according to another aspect of the present invention includes: a light source for irradiating light to particles to be measured; a plurality of photo detectors for detecting light intensities of diffracted/scattered lights caused by the irradiation of the light; and an operation part for receiving light intensity signals outputted from the respective photodetectors and calculating a particle size distribution of the particles based on the fact that a vector s is represented by a predetermined expression including a product of a vector q and a coefficient matrix K, and the operation part is adapted to compute in parallel and calculate at least two parameters among a plurality of first parameters that depend on the particle sizes of the particles and a plurality of second parameters that depend on spread angles of the diffracted/scattered lights, the first and second parameters being used for calculating one element among elements of the coefficient matrix K.

With this configuration, since the operation part is adapted to compute in parallel and calculate at least two parameters among a plurality of first parameters and a plurality of second parameters used for calculating one element among the elements of the coefficient matrix K, it is possible to reduce the time for calculating the coefficient matrix K as compared to a conventional configuration, and therefore it is possible to reduce the time required for calculating the particle size distribution.

In order to further reduce the calculation time of the coefficient matrix K, it is preferable that the operation part computes in parallel and calculates two kinds of the first parameters and two kinds of the second parameters to thereby calculate each of the elements of the coefficient matrix K based on a following Expression (3):

[Equation 3]

$$k(m, \alpha, \theta) = \sum_{n=1}^{N} \frac{2n+1}{n(n+1)} [a(n, m, \alpha) \times \pi(n, \cos\theta) + b(n, m, \alpha) \times \tau(n, \cos\theta)] \quad (3)$$

Here, k is a value of each of the elements of the coefficient matrix K, m is a refractive index of each of the particles to be measured, $\alpha$ is a value associated with each of the particle sizes of the particles to be measured, $\theta$ is a spread angle of diffracted/scattered light, a and b are the first parameters that depend on the refractive index of the particle and particle size, $\pi$ and $\tau$ are the second parameters that depend on the diffracted/scattered lights, and N is a value that represents the last term when the operating part operates a sum represented by a sigma symbol.

Advantageous Effects of Invention

According to the present invention configured as described above, it becomes possible to significantly reduce the calculation time of the coefficient matrix K as compared to the conventional configuration, and therefore it is possible to reduce the time required for entire measurement.

DESCRIPTION OF EMBODIMENTS

The following describes one embodiment of a particle size distribution measuring apparatus 1 according to the present invention with reference to the accompanying drawings.

The particle size distribution measuring apparatus 1 according to the present embodiment is intended to measure a particle size distribution by detecting the diffracted/scattered lights making use of a fact that a light intensity pattern (a light intensity distribution) associated with a spread angle of the diffracted/scattered lights caused upon irradiation of light to the particles is determined by the particle sizes based on Mie scattering theory.

Figure 1:
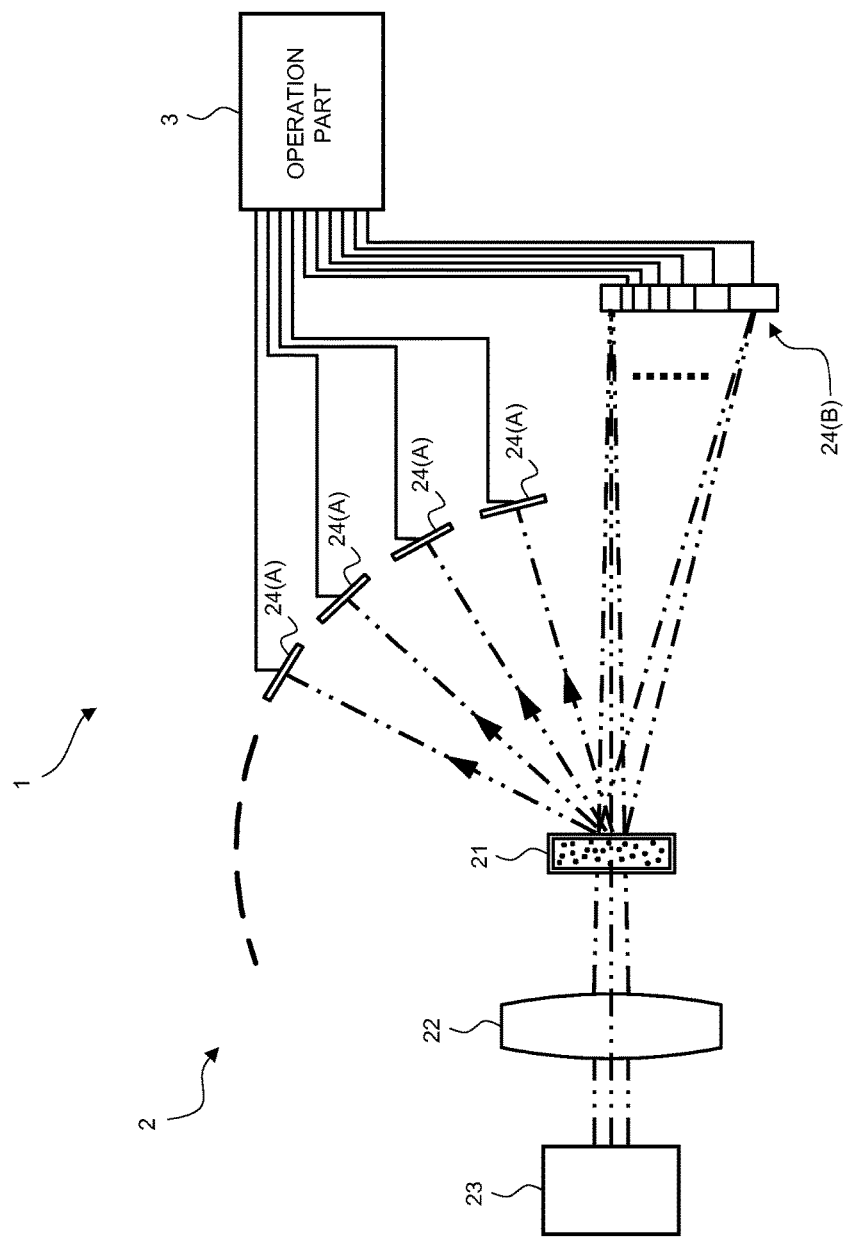
FIG. 1 is a schematic diagram showing a particle size distribution measuring apparatus in one embodiment of the present invention.

As schematically shown in FIG. 1, the particle size distribution measuring apparatus 1 includes an apparatus main body 2 and an operation part 3.

The apparatus main body 2 includes: a cell 21 for accommodating a sample of dispersed particles; a laser device serving as a light source 23 for irradiating laser beams to the particle within the cell 21 through a lens 22; and a plurality of photodetectors 24(A) and 24(B) for detecting light intensities of the diffracted/scattered lights caused by the irradiation of the laser beams associated with the spread angles thereof.

In this configuration, although a batch-type cell is used as the cell 21 in the present embodiment, a circulating cell may be also used.

The operation part 3 is physically configured of a general-purpose or dedicated computer including a CPU, a memory, an input/output interface, and the like, and it is intended to receive light intensity signals outputted from the respective photodetectors 24(A) to 24(B) and calculate a particle size distribution based on Expression (1).

Figure 2:
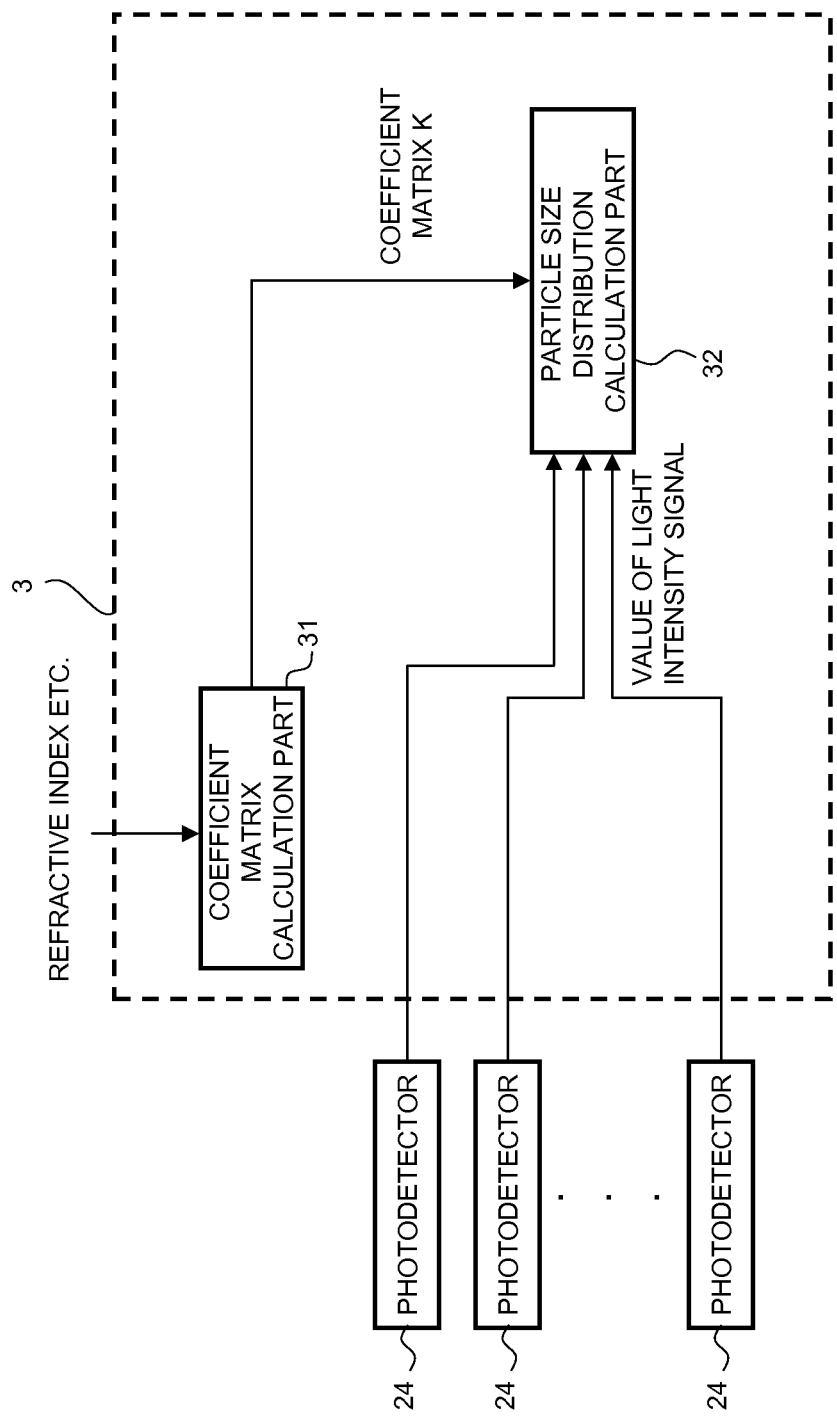
FIG. 2 is a functional block diagram showing a functional configuration of an operation part in the same embodiment.

This operation part 3 is intended to exhibit at least functions of a coefficient matrix calculation part 31 and a particle size distribution calculation part 32 by allowing the CPU and peripherals to cooperate in accordance with a predetermined program stored in a predetermined area of the memory as shown in FIG. 2. More specifically, referring to the functions, the coefficient matrix calculation part 31 is adapted to calculate the coefficient matrix K and the particle size distribution calculation part 32 is adapted to calculate a particle size distribution based on Expression (1) using a light intensity pattern vector s and the coefficient matrix K obtained from values of the respective light intensity signals.

In the present embodiment, since the coefficient matrix calculation part 31 has specific features, these features are described below.

The coefficient matrix calculation part 31 is intended to calculate the coefficient matrix K associated with physical properties of the particles to be measured, particle sizes and arrangement positions of the photodetectors 24. In the present embodiment, the coefficient matrix calculation part 31 is configured to receive values of, for example, refractive indexes of the particles inputted by an operator and calculate each of elements of the coefficient matrix K associated with the particle sizes and the arrangement positions of the photodetectors 24.

Figure 3:
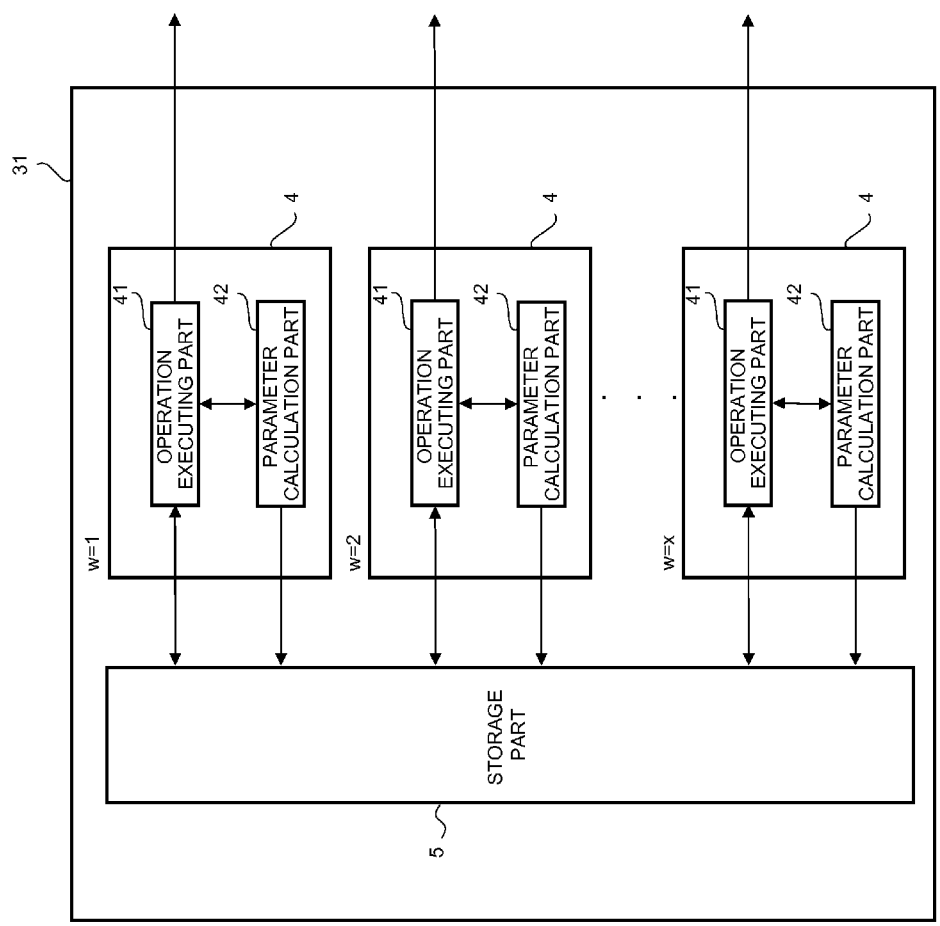
FIG. 3 is a functional block diagram showing a functional configuration of a coefficient matrix calculation part in the same embodiment.

More specifically, as shown in FIG. 3, the coefficient matrix calculation part 31 has functions serving as: a plurality of element calculation parts 4 for calculating the elements based on Expression (3); and a storage part 5 for storing two kinds of first parameters a and b and two kinds of second parameters $\pi$ and $\tau$ that are calculated in a calculation process of each of the element calculation parts 4.

Here, in the present embodiment, the storage part 5 is set in a predetermined area of a cache memory.

As shown in FIG. 3, each of the element calculation parts 4 has functions serving as an operation executing part 41 for executing an operation based on Expression (3) and a parameter calculation part 42 for calculating parameters to be used in an operation executed by the operation executing part 41.

Figure 4:
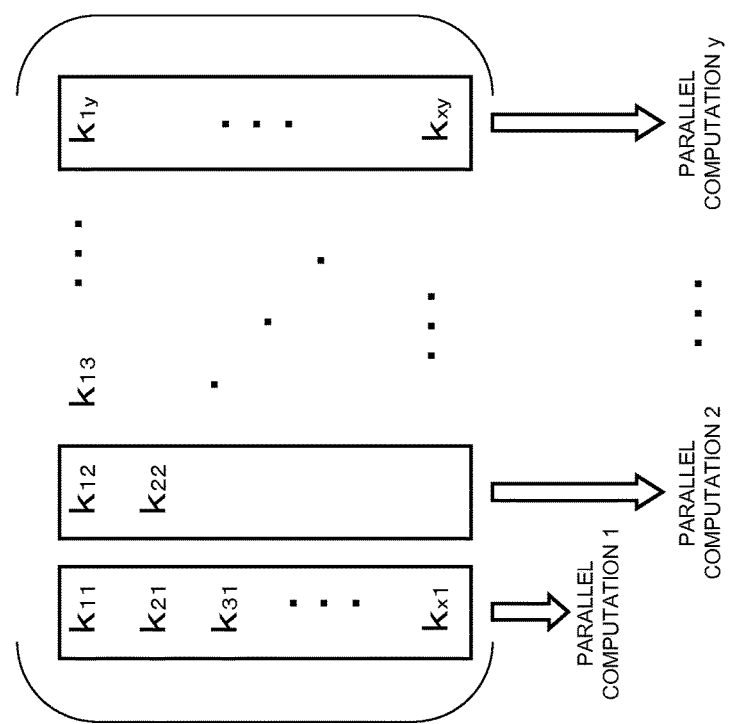
FIG. 4 is a diagram showing a calculation procedure of the coefficient matrix calculation part in the same embodiment.

Thus, in the present embodiment, the coefficient matrix calculation part 31 has the same number of the element calculation parts 4 as the number (x) of the rows of the coefficient matrix K, and as shown in FIG. 4, these element calculation parts 4 are configured so as to compute the elements included in one column in parallel and proceed in sequence this parallel computation from the first column to the last (i.e., y-th) column to thereby calculate all of the elements.

Regarding the parallel computation mentioned here, it is not necessary that starting or ending of the computations and the like are executed at the same timing. That is, it may also include a computation state where each of the element calculation parts 4 calculates the elements with some time lags.

Also, these element calculation parts 4 may be configured so as to be mounted on a plurality of personal computers.

Figure 5:
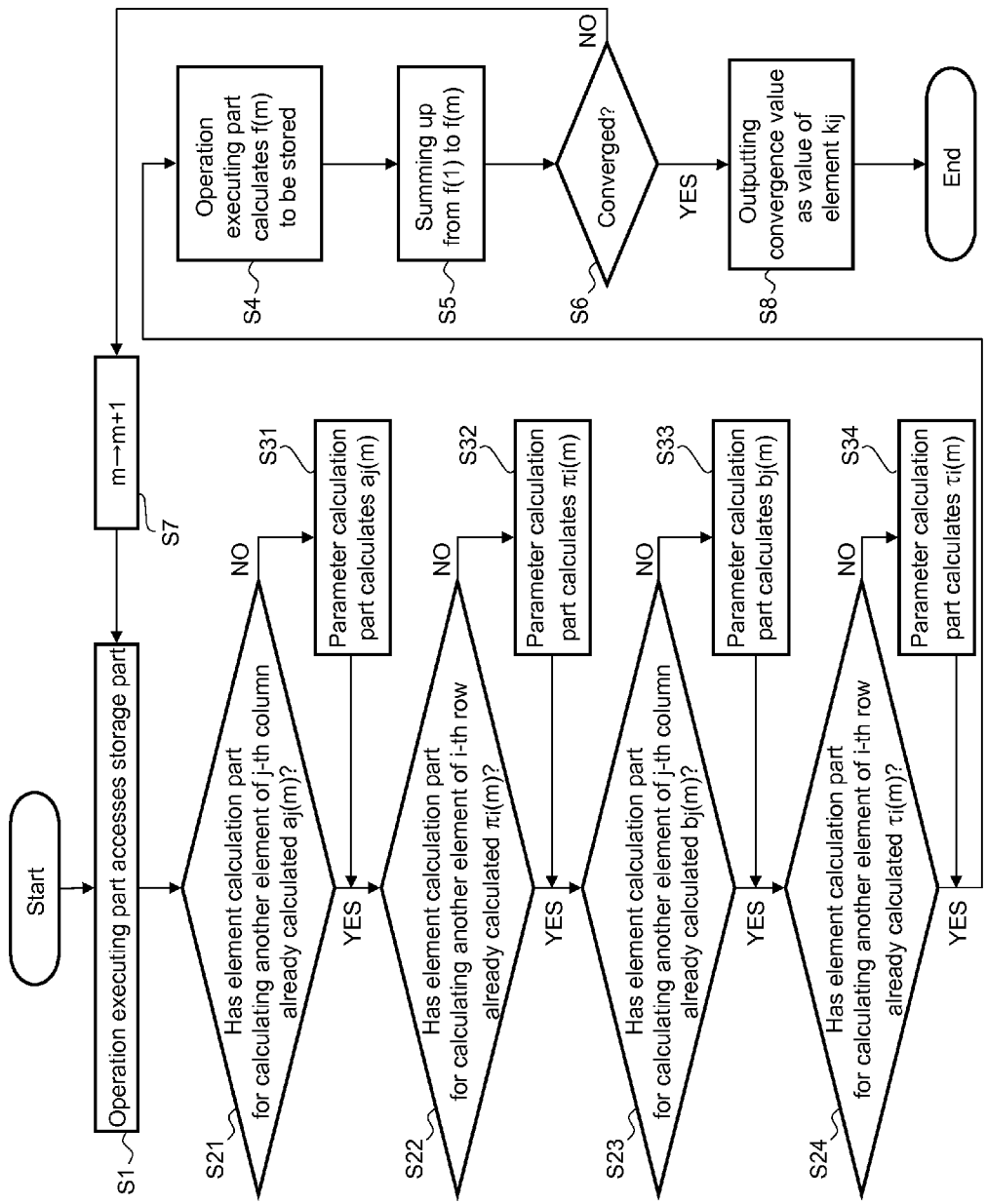
FIG. 5 is a flow chart showing a procedure of calculating an element by an element calculation part in the same embodiment.

Subsequently, a procedure of calculating an element positioned at an intersection of, for example, i-th row and j-th column by the element calculation part 4 is described in detail with reference to FIGS. 3 and 5 together with an explanation of an operation of each part in the element calculation part 4. Here, i is an integer in a range of $1 \leq i \leq x$, and j is an integer in a range of $1 \leq j \leq y$.

In the following description, it is assumed that the refractive index m of the particles is inputted to the coefficient matrix calculation part 31 by the operator.

Here, the element $k_{ij}$ indicates a light intensity detected when the diffracted/scattered light caused by the particles of a unit amount of particles belonging to a j-th range of divided particle size ranges to be measured is incident to the i-th photodetector 24 among the plurality of photodetectors 24. Accordingly, the value $\alpha$ associated with each of the particle sizes and the spread angle $\theta$ of the diffracted/scattered light in Expression (3) represented in obtaining this element $k_{ij}$ become constants, and each of the element calculation parts 4 calculates the element $k_{ij}$, based on the following Expression (3)' including only n as a variable.

[Equation 4]

$$k_{ij} = \sum_{n=1}^{N} \frac{2n+1}{n(n+1)} [a_j(n) \times \pi_i(n) + b_j(n) \times \tau_i(n)], \quad (3)'$$

Here, for convenience of the explanation, Expression (4) is put as following:

[Equation 5]

$$f(n) = \frac{2n+1}{n(n+1)} [a_j(n) \times \pi_i(n) + b_j(n) \times \tau_i(n)] \quad (4)$$

Further, the following describes the case of n=m as an example.

In the present embodiment, there are included a plurality of first parameters of one kind in the above Expressions (3)' and (4) that are respectively represented as $a_j(1)$, $a_j(2)$, ... $a_j(N)$. Similarly, there are also included a plurality of first parameters of two kinds that are respectively represented as $b_j(1)$, $b_j(2)$, ..., $b_j(N)$.

In the present embodiment, there are included a plurality of second parameters of one kind in the above Expressions (3)' and (4) that are respectively represented as $\pi_i(1)$, $\pi_i(2)$, ..., $\pi_i(N)$. Similarly, there are also included a plurality of second parameters of two kinds that are respectively represented as $\tau_i(1)$, $\tau_i(2)$, ..., $\tau_i(N)$.

First, the operation executing part 41 accesses the storage part 5 (Step S1) and confirms whether or not the element calculation part 4 for calculating another element included in j-th column or i-th row has already calculated the parameters $a_j(m)$, $\pi_i(m)$, $b_j(m)$ and $\tau_i(m)$ the values of which are stored in the storage part 5 (Steps S21 to S24).

Regarding the parameters which the element calculation part 4 for calculating another element has already calculated in Steps S21 to S24, the operation executing part 41 acquires the values of the parameters from the storage part 5.

Regarding the parameters which the element calculation part 4 for calculating another element has not yet calculated in Steps S21 to S24, the operation executing part 41 transmits the calculation signal for calculating the parameter to the parameter calculation part 42.

Upon receipt of the calculation signal, the parameter calculation part 42 calculates the value of the parameter corresponding to the calculation signal and transmits the value to the operation executing part 41 as well as to the storage part 5 (Steps S31 to S34).

The operation executing part 41 calculates f(m) using the value of each parameter acquired from the storage part 5 and the parameter calculation part 42 and stores the value in a predetermined area of the memory (Step S4).

Subsequently, the operation executing part 41 acquires the values of f(1) to f(m) and sums these values (Step S5) and determines whether or not the total sum converges to a value (Step S6).

It is noted that the determination of whether or not the total sum converges is performed depending on, for example, whether or not a ratio of the total sum from f(1) to f(m−1) and that from f(1) to f(m) becomes a value or smaller.

In the case where it is determined in Step S6 that the total sum has not yet converged, the process is returned to Step S1 again while putting n=m+1 (Step S7), and the process from Steps S1 to S5 is repeated until it is determined in Step S6 that the total sum converges.

In the case where it is determined in Step S6 that the total sum has converged, the operation executing part 41 takes the convergence value as the value of the element $k_{ij}$ to be outputted to the particle size distribution calculation part (Step S8).

According the particle size distribution measuring apparatus 1 according to the present embodiment configured as described above, the following effects can be obtained.

Since the plurality of element calculation parts 4 compute in parallel and calculate all of the elements included in a certain column and a certain element calculation part 4 transmits the value of the parameter calculated in the computation process to the storage part 5 while another element calculation part 4 acquires the value of this parameter from the storage part 5 to thereby calculate the element, the calculation time of the coefficient matrix K can be remarkably reduced as compared to the conventional case of calculating the elements one by one.

This effect is described in detail below.

Figure 6:
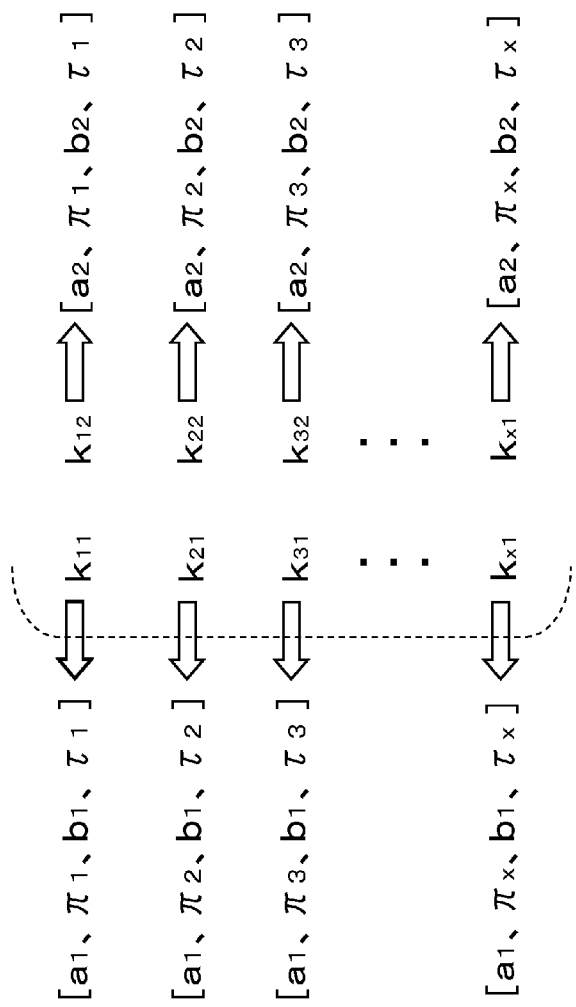
FIG. 6 is a diagram for explaining an effect of the particle size distribution measuring apparatus in the same embodiment.

In the case where the plurality of element calculation parts 4 compute in parallel, for example, the elements of the first column, the two kinds of the first parameters $a_1(n)$ and $b_1(n)$ are used in common for calculating each of the elements as shown in FIG. 6. Therefore, if any one of the plurality of element calculation parts 4 calculates the first parameter $a_1(n)$ or $b_1(n)$, another element calculation part 4 can acquire this value from the storage part 5 to be used for calculating the element.

Subsequently, in the case where the plurality of element calculation parts 4 compute in parallel, for example, the elements of the second column, the two kinds of the second parameters $\pi_i(n)$ and $\tau_i(n)$ have been already calculated in a process of calculating the elements included in the first column. Therefore, each of the element calculation parts 4 acquires the values of the two kinds of the second parameters $\pi_i(n)$ and $\tau_i(n)$ which have been already calculated from the storage part 5 and the acquired values can be used for calculating each of the elements. Similarly, this is also applied to the case of calculating the elements from the third column to the y-th column.

Therefore, as described above, according to the particle size distribution measuring apparatus 1 according to the present embodiment, the time required for calculating each of the elements can be reduced and the calculation time of the coefficient matrix K can be remarkably reduced and the calculation time of the particle size distribution can be reduced compared to the conventional case.

Note that the present invention should not be intended to be limited to the above embodiment.

Figure 7:
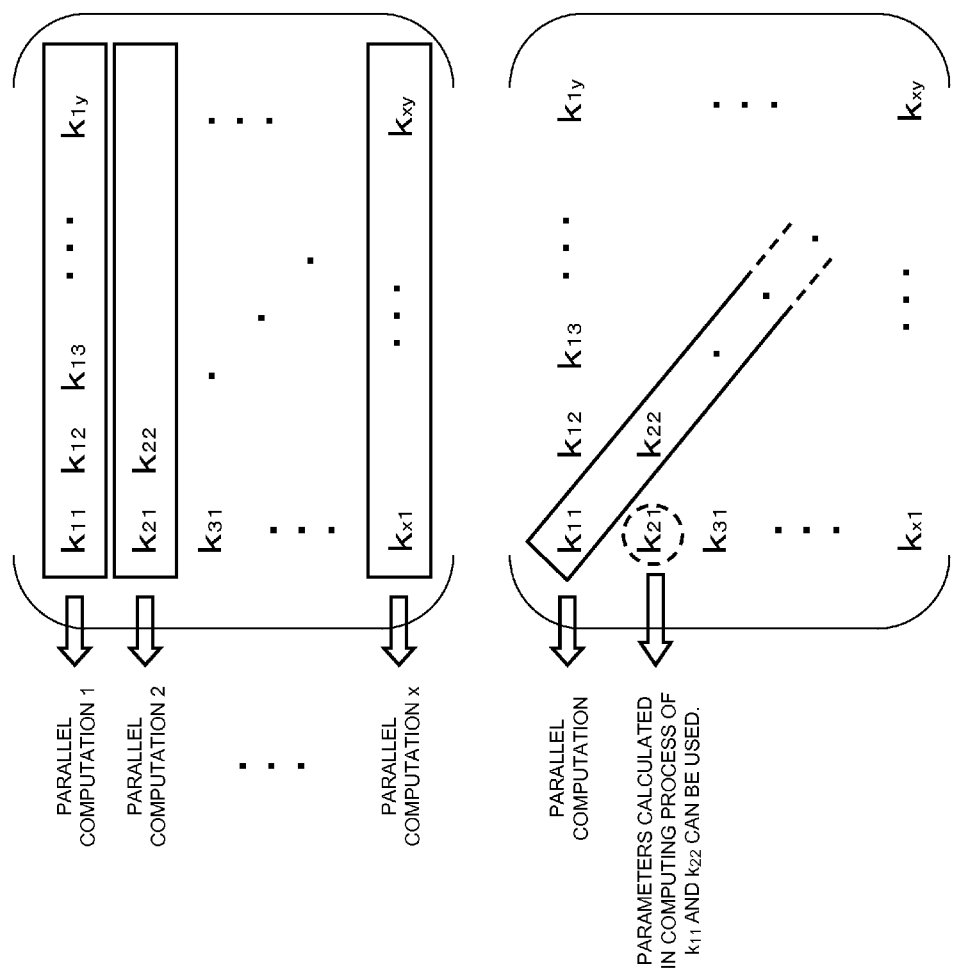
FIG. 7 is a diagram showing a calculation procedure of a coefficient matrix calculation part in another embodiment.

For example, although it is configured to compute in parallel the plurality of elements included in one column in the present embodiment, it may be also configured to compute in parallel the plurality of elements included in one row as shown in an upper part of FIG. 7.

Further, as shown in a lower part of FIG. 7, it may be also configured to compute in parallel the plurality of elements positioned diagonally. Also, in this case, the values of the parameters calculated by computing in parallel the plurality of elements can be used for calculating another element.

Moreover, a computing order of the respective columns can be freely selected and it may be configured to sequentially calculate from the y-th column to the first column. With this configuration, it is possible to calculate in preference the elements which correspond to rearward or sideward diffracted/scattered lights and requiring a relatively long time for converging in Step S6.

Further, in the above embodiment, although the parameter calculation part 42 is configured so as to sequentially calculate the parameters a, π, b and τ, it may be configured so as to compute in parallel at least two kinds of parameters among these parameters to be calculated. Further, it may be configured so as to compute in parallel the same kind of parameters like, for example, one kind of the first parameter $a_j(1)$ and one kind of the first parameter $a_j(2)$.

With this configuration, the calculation time of the coefficient matrix K can be further reduced.

Furthermore, in the above embodiment, although the parameter calculation part 42 transmits all of the calculated values of the parameters to the storage part 5, it may be configured to transmit the values calculated up to a predetermined number of terms (for example, n=100) to the storage part 5 and not to transmit the values thereafter (for example, after n=101) to the storage part 5.

In the above embodiment, although the particle size distribution calculation part 32 is intended to calculate the particle size distribution based on Expression (1), it may be intended to calculate the particle size distribution based on an expression obtained by adding a term representing such as, for example, a noise to this Expression (1).

Further, although the vector s in Expression (1) is a vector representing a light intensity pattern of the diffracted/scattered light obtained from the value of the light intensity signal outputted from each of the photodetectors 24, the vector s may be a vector using the value of the light intensity signal per se as the element.

In this case, in order to convert a vector q representing the particle size distribution to the vector s, each of the elements of the coefficient matrix K may be a value that is obtained by further converting the value obtained from Expression (2) using such as, for example, a distance from each of the photodetectors 24 to the cell 21.

Referring to the apparatus main body 2, although a laser device is used as the light source 23 in the above embodiment, there may be used, for example, an LED element that emits non-deflection light as the light source 23.

In this case, it is only necessary that the element calculation part 4 is configured so as to calculate each of the elements based on a mean value of $k_1$ and $k_2$ obtained from the following two Expressions (5) and (6) that represent a vertical deflection component and a horizontal deflection component of the light intensity.

[Equation 6]

$$k_1(m, \alpha, \theta) = \sum_{n=1}^{N} \frac{2n+1}{n(n+1)}[a(n, m, \alpha) \times \pi(n, \cos\theta) + b(n, m, \alpha) \times \tau(n, \cos\theta)] \quad (5)$$

$$k_2(m, \alpha, \theta) = \sum_{n=1}^{N} \frac{2n+1}{n(n+1)}[a(n, m, \alpha) \times \pi(n, \cos\theta) + b(n, m, \alpha) \times \tau(n, \cos\theta)] \quad (6)$$

Note that this Expression (5) is identical to Expression (2) and this expression can be used in common even if the light from the light source 23 is deflection light or non-deflection light.

In addition, the present invention should not be limited to the above embodiment and each of the partial components can be combined, and various modifications are of course possible within the scope unless departing from the intended spirit thereof.

REFERENCE SIGNS LIST

1 . . . Particle size distribution measuring apparatus
2 . . . Apparatus body
3 . . . Operation part
31 . . . Coefficient matrix calculation part
4 . . . Element calculation part
41 . . . Operation executing part
42 . . . Parameter calculation part
5 . . . Storage part

The invention claimed is:

1. A particle size distribution measuring apparatus comprising:
   a light source structured for irradiating light to particles to be measured;
   a plurality of photodetectors structured for detecting light intensities of diffracted/scattered lights caused by the irradiation of the light, and output light intensity signals; and
   a computer configured to:
      calculate a vector s representing a light intensity pattern at every angle of the diffracted/scattered lights based on the light intensity signals output by the plurality of photodetectors;
      calculate a coefficient matrix K;
      calculate a vector q representing the particle size distribution of the particles to be measured, based on the vector s and the coefficient matrix K;
   wherein the coefficient matrix K comprises a plurality of elements;
   wherein the computer is configured to calculate the plurality of elements by using first parameters that depend on particle size and second parameters that depend on the diffracted/scattered lights;
   wherein the computer is further configured to calculate the plurality of elements such that at least two of the plurality of elements of the coefficient matrix K are computed in parallel.

2. The particle size distribution measuring apparatus according to claim 1, wherein the at least two elements of elements of the coefficient matrix K are elements included in one row or elements included in one column of the coefficient matrix K.

3. The particle size distribution measuring apparatus according to claim 1, wherein the computer is configured to calculate values of a plurality of parameters used for calculating one element of the coefficient matrix K and to store the values to be used for calculating another element of the coefficient matrix K.

4. The particle size distribution measuring apparatus according to claim 1, wherein the computer is configured to calculate an element of a position where a certain row and a certain column intersect in coefficient matrix K using the values of the plurality of parameters stored at a time of calculating the elements included in the row and the values of the plurality of parameters stored, at a time of calculating the elements included in the column among the elements of the coefficient matrix K.

5. A particle size distribution measuring apparatus comprising:
   a light source structured for irradiating light to particles to be measured;
   a plurality of photodetectors structured for detecting light intensities of diffracted/scattered lights caused by the irradiation of the light, and output light intensity signals; and
   a computer configured to
      calculate a vector s representing a light intensity pattern at every angle of the diffracted/scattered lights based on the light intensity signals output by the plurality of photodetectors;
      calculate a coefficient matrix K;
      calculate a vector q representing the particle size distribution of the particles to be measured, based on the vector s and the coefficient matrix K;
   wherein the coefficient matrix K comprises a plurality of elements;
   wherein the computer is configured to calculate the plurality of elements by using first parameters that depend on particle size and second parameters that depend on the diffracted/scattered lights;
   wherein each element of the plurality of elements is calculated based on a plurality of first parameters that depend on particle sizes of the particles to be measured and a plurality of second parameters that depend on spread angles of diffracted/scattered lights;
   wherein the computer is further configured to calculate the plurality of first parameters and plurality of second parameters such that at least two parameters among the plurality of first parameters and plurality of second parameters are computed in parallel.

6. The particle size distribution measuring apparatus according to claim 5, wherein the computer is configured to compute in parallel and calculate two kinds of the first parameters and two kinds of the second parameters to thereby calculate each of the elements of the coefficient matrix K based on a following expression:

$$k(m, \alpha, \theta) = \sum_{n=1}^{N} \frac{2n+1}{n(n+1)} [a(n, m, \alpha) \times \pi(n, \cos\theta) + b(n, m, \alpha) \times \tau(n, \cos\theta)]$$

wherein k is a value of each of the elements of the coefficient matrix K, m is a refractive index of each of the particles to be measured, α is a value associated with each of the particle sizes of the particles to be measured, θ is a spread angle of diffracted/scattered light, a and b are the first parameters that depend on the refractive index of the particle and particle size, π and τ are the second parameters that depend on the diffracted/scattered lights, and N is a value that represents the last term when the operating part operates a sum represented by a sigma symbol.

7. A non-transitory recording medium recorded with a program for execution on a particle size distribution measuring apparatus comprising a light source structured for irradiating light to particles to be measured; a plurality of photodetectors structured for detecting light intensities of diffracted/scattered lights caused by the irradiation of the light, and output light intensity signals; and a computer, the program, when executed on the computer, causes the computer to:

calculate a vector s representing a light intensity pattern at every angle of the diffracted/scattered lights based on the light intensity signals output by the plurality of photodetectors;

calculate a coefficient matrix K;

calculate a vector q representing the particle size distribution of the particles to be measured, based on the vector s and the coefficient matrix K;

wherein the coefficient matrix K comprises a plurality of elements;

wherein the plurality of elements are calculated by using first parameters that depend on particle size and second parameters that depend on the diffracted/scattered lights;

wherein at least two of the plurality of elements of the coefficient matrix K are computed in parallel.

* * * * *